(12) United States Patent
Sakakibara et al.

(10) Patent No.: US 8,697,331 B2
(45) Date of Patent: Apr. 15, 2014

(54) COMPOUND, POLYMER, AND RADIATION-SENSITIVE COMPOSITION

(75) Inventors: Hirokazu Sakakibara, Tokyo (JP); Takehiko Naruoka, Tokyo (JP); Makoto Shimizu, Tokyo (JP); Yukio Nishimura, Tokyo (JP); Nobuji Matsumura, Tokyo (JP); Yuusuke Asano, Tokyo (JP)

(73) Assignee: JSR Corporation, Tokyo (JP)

( * ) Notice: Subject to any disclaimer, the term of this patent is extended or adjusted under 35 U.S.C. 154(b) by 21 days.

(21) Appl. No.: 12/949,795

(22) Filed: Nov. 19, 2010

(65) Prior Publication Data

US 2011/0104611 A1 May 5, 2011

Related U.S. Application Data

(63) Continuation of application No. PCT/JP2009/059152, filed on May 18, 2009.

(30) Foreign Application Priority Data

May 19, 2008 (JP) .................... 2008-131255

(51) Int. Cl.
  *G03F 7/004* (2006.01)
  *G03F 7/039* (2006.01)

(52) U.S. Cl.
  USPC ...................... 430/270.1; 430/910

(58) Field of Classification Search
  USPC .............. 430/270.1, 326, 910; 526/245
  See application file for complete search history.

(56) References Cited

U.S. PATENT DOCUMENTS

| | | | | |
|---|---|---|---|---|
| 7,014,980 | B2 * | 3/2006 | Allen et al. ............... | 430/270.1 |
| 7,312,288 | B2 * | 12/2007 | Kinsho et al. ............. | 526/245 |
| 2002/0061466 | A1 | 5/2002 | Lee et al. | |
| 2003/0078352 | A1 * | 4/2003 | Miyazawa et al. ........ | 526/245 |
| 2005/0208419 | A1 | 9/2005 | Inabe et al. | |
| 2006/0194143 | A1 * | 8/2006 | Sumida et al. ............ | 430/270.1 |
| 2006/0216643 | A1 * | 9/2006 | Li et al. .................... | 430/270.1 |
| 2007/0172769 | A1 * | 7/2007 | Kanna et al. .............. | 430/311 |
| 2007/0179309 | A1 | 8/2007 | Hasegawa et al. | |
| 2009/0011365 | A1 * | 1/2009 | Kobayashi et al. ....... | 430/284.1 |
| 2010/0255420 | A1 * | 10/2010 | Sakakibara et al. ....... | 430/285.1 |

FOREIGN PATENT DOCUMENTS

| | | |
|---|---|---|
| CN | 1930523 | 3/2007 |
| JP | 2002-220416 | 8/2002 |
| JP | 2005-173474 | 6/2005 |
| JP | 2006-048029 | 2/2006 |
| JP | 2006-079048 | 3/2006 |
| JP | 2007-204385 | 8/2007 |
| WO | WO 2004/068242 | 8/2004 |
| WO | WO 2009/057484 | 5/2009 |

OTHER PUBLICATIONS

International Preliminary Report on Patentability with Translation of Written Opinion of the International Searching Authority for corresponding International Application No. PCT/JP2009/059152, Aug. 11, 2009.

Chinese Office Action for corresponding CN Application No. 200980117928.5, Dec. 21, 2011.

* cited by examiner

*Primary Examiner* — Anca Eoff
(74) *Attorney, Agent, or Firm* — Ditthavong Mori & Steiner, P.C.

(57) ABSTRACT

A compound is shown by a following formula (1), $$H_2C=C\begin{matrix}R^1\\|\\C\end{matrix}\begin{matrix}=O\\|\\O-R^2-X-O-\underset{\underset{O}{\|}}{C}-O-C(R^3)(R^3)R^3\end{matrix}\tag{1}$$

wherein $R^1$ represents a hydrogen atom, a methyl group, or a trifluoromethyl group, $R^2$ represents a methylene group, an ethylene group, a 1-methylethylene group, a 2-methylethylene group, a divalent alicyclic hydrocarbon group having 4 to 20 carbon atoms, or a derivative thereof, each of $R^3$ represents at least one of a monovalent alicyclic hydrocarbon group having 4 to 20 carbon atoms, a derivative thereof, and a linear or branched alkyl group having 1 to 4 carbon atoms, provided that two of $R^3$ may bond to form a divalent alicyclic hydrocarbon group having 4 to 20 carbon atoms or a derivative thereof together with the carbon atom that is bonded thereto, and X represents a linear or branched fluoroalkylene group having 1 to 20 carbon atoms.

7 Claims, 1 Drawing Sheet

COMPOUND, POLYMER, AND RADIATION-SENSITIVE COMPOSITION

CROSS-REFERENCE TO RELATED APPLICATIONS

The present application is a continuation application of International Application No. PCT/JP2009/059152, filed May 18, 2009, which claims priority to Japanese Patent Application No. 2008-131255, filed May 19, 2008. The contents of these applications are incorporated herein by reference in their entirety

BACKGROUND OF THE INVENTION

1. Field of the Invention

The present invention relates to a compound, a polymer, and a radiation-sensitive composition.

2. Discussion of the Background

In the field of microfabrication represented by production of integrated circuit devices, lithographic technology that enables microfabrication with a line width of 0.10 μm or less has been desired to achieve a higher degree of integration.

A lithographic process has utilized near ultraviolet rays (e.g., i-line). However, it is difficult to implement sub-quarter-micron microfabrication using near ultraviolet rays.

Therefore, use of radiation having a shorter wavelength has been studied to enable microfabrication with a line width of 0.10 μm or less. Examples of such radiation include deep ultraviolet rays (e.g., mercury line spectrum and excimer laser light), X-rays, electron beams, and the like. In particular, technology that utilizes KrF excimer laser light (wavelength: 248 nm) or ArF excimer laser light (wavelength: 193 nm) has attracted attention.

As a resist that is suitable for excimer laser light, various resists (chemically-amplified resists) that utilize a chemical amplification effect due to an acid-dissociable functional group-containing component and a component that generates an acid upon irradiation (exposure) (hereinafter referred to as "acid generator") have been proposed.

For example, a chemically-amplified resist that includes a resin containing a t-butyl ester group of a carboxylic acid or a t-butyl carbonate group of phenol, and an acid generator has been proposed. This resist utilizes a phenomenon in which the t-butyl ester group or the t-butyl carbonate group contained in the resin dissociates due to an acid generated upon exposure to form an acidic group (e.g., carboxyl group or phenolic hydroxyl group), so that the exposed area of the resist film becomes readily soluble in an alkaline developer.

Such a lithographic process will be required to form a finer pattern (e.g., a resist pattern with a line width of about 90 nm). A pattern having a line width of less than 90 nm may be formed by reducing the wavelength of the light source of the exposure system, or increasing the numerical aperture (NA) of the lens.

However, since a new exposure system is required to reduce the wavelength of the light source, the equipment cost increases. When increasing the numerical aperture (NA) of the lens, since the resolution and the depth of focus have a trade-off relationship, a decrease in depth of focus occurs when increasing the resolution.

In recent years, liquid immersion lithography has been proposed as lithographic technology that can solve the above problems. In liquid immersion lithography, a liquid refractive medium (immersion liquid) (e.g., purified water or fluorine-containing inert liquid) is interposed (at least over the resist film) between the lens and the resist film formed on the substrate during exposure.

According to liquid immersion lithography, the optical space (path) is filled with a liquid (e.g., pure water) having a high refractive index (n) instead of an inert gas (e.g., air or nitrogen) so that the resolution can be increased without causing a decrease in depth of focus in the same manner as in the case of using a short-wavelength light source or a high NA lens. A resist pattern that exhibits excellent resolution and an excellent depth of focus can be inexpensively formed by liquid immersion lithography using a lens provided in an existing system. A polymer, an additive, and the like for forming a resist used for liquid immersion lithography have been proposed (see WO2004/068242, Japanese Patent Application Publication (KOKAI) No. 2005-173474, and Japanese Patent Application Publication (KOKAI) No. 2006-48029, for example).

However, liquid immersion lithography has a problem in that the acid generator and the like are eluted from the resist film when the resist film directly comes in contact with the immersion liquid (e.g., water) during exposure. If the elution volume is large, the lens may be damaged, or the desired pattern shape or sufficient resolution may not be obtained.

When using water as the immersion liquid, if the receding contact angle formed by the resist film and water is low, the immersion liquid may drip from the edge of the wafer during high-speed scanning exposure, or development defects such as watermark defects (i.e., a watermark remains) or blob defects (i.e., the solubility of the resist film decreases due to water permeation so that the pattern locally remains unresolved (i.e., an excellent pattern shape is not obtained)) may occur.

Moreover, the receding contact angle formed by the resist film and water is not necessarily sufficient when using a resist including the resin and the additive disclosed in WO2004/068242, Japanese Patent Application Publication (KOKAI) No. 2005-173474, and Japanese Patent Application Publication (KOKAI) No. 2006-48029. If the receding contact angle is low, the immersion liquid (e.g., water) may drip from the edge of the wafer during high-speed scanning exposure, or development defects such as watermark defects may occur. Furthermore, elution of the acid generator and the like into water is not necessarily sufficiently suppressed.

SUMMARY OF THE INVENTION

According to one aspect of the present of the invention, a compound is shown by a following formula (1), wherein $R^1$ represents a hydrogen atom, a methyl group, or a trifluoromethyl group, $R^2$ represents a methylene group, an ethylene group, a 1-methylethylene group, a 2-methylethylene group, a divalent alicyclic hydrocarbon group having 4 to 20 carbon atoms, or a derivative thereof, each of $R^3$ represents at least one of a monovalent alicyclic hydrocarbon group having 4 to 20 carbon atoms, a derivative thereof, and a linear or branched alkyl group having 1 to 4 carbon atoms, provided that two of $R^3$ may bond to form a divalent alicyclic hydrocarbon group having 4 to 20 carbon atoms or a derivative thereof together with the carbon atom that is bonded thereto, and X represents a linear or branched fluoroalkylene group having 1 to 20 carbon atoms.

According to another aspect of the present of the invention, a fluorine-containing polymer includes a first repeating unit derived from the above compound According to further of the present of the invention, a radiation-sensitive composition includes the above fluorine-containing polymer and a solvent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments of the invention are described with reference to the accompanying drawings, wherein like reference numerals designate corresponding or identical elements throughout the various drawings. Note that the invention is not limited to the following embodiments. Various modifications, improvements, and the like may be appropriately made of the design without departing from the scope of the invention based on common knowledge of a person skilled in the art.

Note that the term "(meth)acryl" refers to either or both of "acryl" and "methacryl".

[1] Radiation-Sensitive Composition

A radiation-sensitive composition according to an embodiment of the invention is described in detail below. A radiation-sensitive composition according to one embodiment of the invention includes a fluorine-containing polymer (hereinafter may be referred to as "fluorine-containing polymer (A)") that includes a repeating unit (1) derived from a compound shown by the following general formula (1) (hereinafter may be referred to as "compound (1)"), and a solvent.

wherein $R^1$ represents a hydrogen atom, a methyl group, or a trifluoromethyl group, $R^2$ represents a methylene group, an ethylene group, a 1-methylethylene group, a 2-methylethylene group, a divalent alicyclic hydrocarbon group having 4 to 20 carbon atoms, or a derivative thereof, $R^3$ individually represent a monovalent alicyclic hydrocarbon group having 4 to 20 carbon atoms, a derivative thereof, or a linear or branched alkyl group having 1 to 4 carbon atoms, provided that two of $R^3$ may bond to form a divalent alicyclic hydrocarbon group having 4 to 20 carbon atoms or a derivative thereof together with the carbon atom that is bonded thereto, and X represents a linear or branched fluoroalkylene group having 1 to 20 carbon atoms.

The radiation-sensitive composition according to one embodiment of the invention includes the novel fluorine-containing polymer (A) that includes the repeating unit (1) derived from the novel compound (1), and may suitably be used to form a resist film in a resist pattern-forming method that includes liquid immersion lithography that applies radiation via an immersion liquid (e.g., water) that has a refractive index higher than that of air at a wavelength of 193 nm and is positioned between a lens and a resist film. A resist film formed using the radiation-sensitive composition produces an excellent pattern shape, reduces the elution volume upon contact with an immersion liquid (e.g., water) during liquid immersion lithography, ensures that a high receding contact angle is formed by the resist film and an immersion liquid (e.g., water), and rarely causes development defects.

Note that the term "receding contact angle" used herein refers to a contact angle formed by a liquid surface and a substrate when dripping 25 μl of water onto a substrate on which a film (resist film) is formed, and sucking the water on the substrate at a rate of 10 μl/min. The receding contact angle may be measured using a contact angle meter ("DSA-10" manufactured by KRUS), for example.

The radiation-sensitive composition according to one embodiment of the invention preferably further includes (B) an acid-labile group-containing polymer differing from the fluorine-containing polymer (A). This makes it possible to advantageously increases the receding contact angle, reduce the elution volume, and suppress development defects, for example. Note that the fluorine-containing polymer (A) may be referred to as "polymer (A)", and the acid-labile group-containing polymer (B) may be referred to as "polymer (B)".

The radiation-sensitive composition according to one embodiment of the invention may include the fluorine-containing polymer (A) as a resist additive. When the radiation-sensitive composition includes the fluorine-containing polymer (A) as an additive, the radiation-sensitive composition preferably includes the fluorine-containing polymer (A) in an amount of 50 parts by mass or less, more preferably 0.1 to 40 parts by mass, and still more preferably 0.5 to 35 parts by mass, based on 100 parts by mass of the polymer (B). If the amount of the fluorine-containing polymer (A) is less than 0.1 parts by mass, the effect of the fluorine-containing polymer (A) may not be obtained, so that the receding contact angle of the resulting resist film may decrease. If the amount of the fluorine-containing polymer (A) is more than 50 parts by mass, a rectangular resist pattern may not be obtained, or the depth of focus may decrease.

[1-1] Compound (1)

The compound (1) that is a monomer component of the fluorine-containing polymer (A) is described below. The compound (1) is shown by the general formula (1). Since the compound (1) includes a specific fluoroalkylene group in the molecule, the receding contact angle formed by the resist film and an immersion liquid can be sufficiently increased. Moreover, it is possible to reduce the elution volume upon contact with an immersion liquid (e.g., water) during liquid immersion lithography, and suppress occurrence of watermark (W/M) defects and bubble defects due to liquid immersion lithography.

Examples of the alicyclic hydrocarbon group having 4 to 20 carbon atoms represented by $R^2$ in the general formula (1) include a divalent hydrocarbon group that includes an alicyclic ring derived from a cycloalkane such as cyclobutane, cyclopentane, cyclohexane, bicyclo[2.2.1]heptane, bicyclo[2.2.2]octane, tricyclo[5.2.1.0$^{2,6}$]decane, tetracyclo[6.2.1.1$^{3,6}$.0$^{2,7}$]dodecane, or tricycle[3.3.1.1$^{3,7}$]decane.

The alicyclic hydrocarbon group represented by $R^2$ may be a derivative obtained by substituting at least one hydrogen atom of the unsubstituted alicyclic hydrocarbon group with at least one of a linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, a hydroxyl group, a cyano group, a hydroxyalkyl group having 1 to 10 carbon atoms, a carboxyl group, an oxygen atom, and the like.

Examples of the monovalent alicyclic hydrocarbon group having 4 to 20 carbon atoms represented by $R^3$ in the general formula (1) include a group that includes an alicyclic ring derived from a cycloalkane such as norbornane, tricyclodecane, tetracyclododecane, adamantane, cyclobutane, cyclopentane, cyclohexane, cycloheptane, or cyclooctane, and the like.

Examples of the derivative of the alicyclic hydrocarbon group represented by $R^3$ include a group obtained by substituting the above monovalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Among these, an alicyclic hydrocarbon group that includes an alicyclic ring derived from norbornane, tricyclodecane, tetracyclododecane, adamantane, cyclopentane, or cyclohexane, a group obtained by substituting the alicyclic hydrocarbon group with the above alkyl group, and the like are preferable.

Examples of the divalent alicyclic hydrocarbon group having 4 to 20 carbon atoms that is formed by two of $R^3$ together with the carbon atom bonded thereto (i.e., the carbon atom bonded to the oxygen atom) include monocyclic hydrocarbon groups such as a cyclobutylene group, a cyclopentylene group, a cyclohexylene group, and a cyclooctylene group, polynuclear hydrocarbon groups such as a norbornylane group, a tricyclodecanylene group, and a tetracyclodecanylene group, and crosslinked polycyclic hydrocarbon groups such as an adamantylene group.

Examples of the derivative of the divalent alicyclic hydrocarbon group formed by two of $R^3$ include a group obtained by substituting the above divalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like. Among these, a cyclopentylene group, a cyclohexylene group, a group obtained by substituting a cyclopentylene group or a cyclohexylene group with the above alkyl group, and the like are preferable.

Examples of the linear or branched alkyl group having 1 to 4 carbon atoms represented by $R^3$ in the general formula (1) include a methyl group, an ethyl group, an n-propyl group, an i-propyl group, an n-butyl group, a 2-methylpropyl group, a 1-methylpropyl group, a t-butyl group, and the like.

Preferable examples of —C($R^3$)$_3$ in the general formula (1) include a t-butyl group, a 1-n-(1-ethyl-1-methyl)propyl group, a 1-n-(1,1-dimethyl)propyl group, a 1-n-(1,1-dimethyl)butyl group, a 1-n-(1,1-dimethyl)pentyl group, 1-(1,1-diethyl)propyl group, a 1-n-(1,1-diethyl)butyl group, a 1-n-(1,1-diethyl)pentyl group, a 1-(1-methyl)cyclopentyl group, a 1-(1-ethyl)cyclopentyl group, a 1-(1-n-propyl)cyclopentyl group, a 1-(1-i-propyl)cyclopentyl group, a 1-(1-methyl)cyclohexyl group, a 1-(1-ethyl)cyclohexyl group, a 1-(1-n-propyl)cyclohexyl group, a 1-(1-i-propyl)cyclohexyl group, a 1-[1-methyl-1-(2-norbornyl)]ethyl group, a 1-[1-methyl-1-(2-tetracyclodecanyl)]ethyl group, a 1-[1-methyl-1-(1-adamantyl)]ethyl group, a 2-(2-methyl)norbornyl group, a 2-(2-ethyl)norbornyl group, a 2-(2-n-propyl)norbornyl group, a 2-(2-i-propyl)norbornyl group, a 2-(2-methyl)tetracyclodecanyl group, a 2-(2-ethyl)tetracyclodecanyl group, a 2-(2-n-propyl)tetracyclodecanyl group, a 2-(2-i-propyl)tetracyclodecanyl group, a 1-(1-methyl)adamantyl group, a 1-(1-ethyl)adamantyl group, a 1-(1-n-propyl)adamantyl group, a 1-(1-i-propyl)adamantyl group, a group obtained by substituting the above group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Examples of the derivative include a group obtained by substituting the above monovalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Among these, an alicyclic hydrocarbon group that includes an alicyclic ring derived from norbornane, tricyclodecane, tetracyclododecane, adamantane, cyclopentane, or cyclohexane, a group obtained by substituting the alicyclic hydrocarbon group with the above alkyl group, and the like are preferable.

X in the general formula (1) represents a linear or branched fluoroalkylene group having 1 to 20 carbon atoms. X preferably represents any of the fluoroalkylene groups shown by the following formulas (X-1) to (X-8). Among these, a ditrifluoromethylene group is particularly preferable.

(X-1)

(X-2)

(X-3)

(X-4)

(X-5)

(X-6)

(X-7)

(X-8)

[1-2] Fluorine-Containing Polymer (A)

The fluorine-containing polymer used for the radiation-sensitive composition according to one embodiment of the invention includes the repeating unit (1) derived from the compound shown by the general formula (1). The fluorine-containing polymer (A) preferably has a receding contact angle of 70° or more, more preferably 72° or more, and still more preferably 75° or more.

It is preferable that the fluorine-containing polymer (A) further include a repeating unit shown by the following general formula (2) (hereinafter may be referred to as "repeating unit (2)").

(2)

wherein $R^4$ represents a hydrogen atom, a methyl group, or a trifluoromethyl group, and $R^5$ individually represent a monovalent alicyclic hydrocarbon group having 4 to 20 carbon atoms, a derivative thereof, or a linear or branched alkyl group having 1 to 4 carbon atoms, provided that two of $R^5$ may bond to form a divalent alicyclic hydrocarbon group having 4 to 20 carbon atoms or a derivative thereof together with the carbon atom that is bonded thereto.

Examples of the monovalent alicyclic hydrocarbon group having 4 to 20 carbon atoms represented by $R^5$ in the general formula (2) include a group that includes an alicyclic ring derived from a cycloalkane such as norbornane, tricyclodecane, tetracyclododecane, adamantane, cyclobutane, cyclopentane, cyclohexane, cycloheptane, or cyclooctane, and the like.

Examples of the derivative of the alicyclic hydrocarbon group represented by $R^5$ include a group obtained by substituting the above monovalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Among these, an alicyclic hydrocarbon group that includes an alicyclic ring derived from norbornane, tricyclodecane, tetracyclododecane, adamantane, cyclopentane, or cyclohexane, a group obtained by substituting the alicyclic hydrocarbon group with the above alkyl group, and the like are preferable.

Examples of the divalent alicyclic hydrocarbon group having 4 to 20 carbon atoms that is formed by two of $R^5$ together with the carbon atom that is bonded thereto (i.e., the carbon atom bonded to the oxygen atom) include monocyclic hydrocarbon groups such as a cyclobutylene group, a cyclopentylene group, a cyclohexylene group, and a cyclooctylene group, polynuclear hydrocarbon groups such as a norbornylane group, a tricyclodecanylene group, and a tetracyclodecanylene group, and crosslinked polycyclic hydrocarbon groups such as an adamantylene group.

Examples of the derivative of the divalent alicyclic hydrocarbon group include a group obtained by substituting the divalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Among these, monocyclic hydrocarbon groups such as a cyclopentylene group, a cyclohexylene group, and a cyclooctylene group, a group obtained by substituting the divalent alicyclic hydrocarbon group (monocyclic hydrocarbon group) with the above alkyl group, and the like are preferable.

Examples of the linear or branched alkyl group having 1 to 4 carbon atoms represented by $R^5$ include a methyl group, an ethyl group, an n-propyl group, an i-propyl group, an n-butyl group, a 2-methylpropyl group, a 1-methylpropyl group, a t-butyl group, and the like.

Preferable examples of —$C(R^5)_3$ in the general formula (2) include the groups mentioned above as preferable examples of —$C(R^3)_3$ in the general formula (1).

The fluorine-containing polymer (A) may include only one type of repeating unit (2), or may include two or more types of repeating unit (2).

The fluorine-containing polymer (A) may further include an additional repeating unit other than the repeating units (1) and (2).

Examples of the additional repeating unit include (i) a repeating unit that includes a lactone skeleton, a hydroxyl group, a carboxyl group, or the like that improves alkali solubility, (ii) a repeating unit that includes an aromatic hydrocarbon group or a derivative thereof that suppresses reflection from a substrate, (iii) a repeating unit that includes an aromatic hydrocarbon group, a derivative thereof, an alicyclic hydrocarbon group, or a derivative thereof that improves etching resistance, and the like. Among these, a repeating unit that includes a lactone skeleton and a repeating unit that includes an alicyclic hydrocarbon group or a derivative thereof are preferable.

Examples of a preferable monomer that produces the repeating unit that includes a lactone skeleton (hereinafter may be referred to as "repeating unit (3)") include monomers shown by the following general formulas (3-1) to (3-6), and the like.

(3-1)

(3-2)

(3-3)

(3-4)

(3-5)

(3-6)

wherein $R^6$ represents a hydrogen atom or a methyl group, $R^7$ represents a hydrogen atom or a substituted or unsubstituted alkyl group having 1 to 4 carbon atoms, $R^8$ represents a hydrogen atom or a methoxy group, A represents a single bond, an ether group, an ester group, a carbonyl group, a divalent chain-like hydrocarbon group having 1 to 30 carbon atoms, a divalent alicyclic hydrocarbon group having 3 to 30 carbon atoms, a divalent aromatic hydrocarbon group having 6 to 30 carbon atoms, or a divalent group that is a combination of these groups, B represents an oxygen atom or a methylene group, i is an integer from 1 to 3, and m is 0 or 1.

Examples of the substituted or unsubstituted alkyl group having 1 to 4 carbon atoms represented by $R^7$ in the general formula (3-1) include a methyl group, an ethyl group, an n-propyl group, an i-propyl group, an n-butyl group, a 2-methylpropyl group, a 1-methylpropyl group, a t-butyl group, and the like.

Examples of the divalent chain-like hydrocarbon group having 1 to 30 carbon atoms represented by A in the general formulas (3-2) and (3-3) include linear alkylene groups such as a methylene group, an ethylene group, a 1,2-propylene group, a 1,3-propylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, and an icosylene group; branched alkylene groups such as a 1-methyl-1,3-propylene group, a 2-methyl-1,3-propylene group, a 2-methyl-1,2-propylene group, a 1-methyl-1,4-butylene group, a 2-methyl-1,4-butylene group, a methylidene group, an ethylidene group, a propylidene group, and a 2-propylidene group; and the like.

Examples of the divalent alicyclic hydrocarbon group having 3 to 30 carbon atoms represented by A in the general formulas (3-2) and (3-3) include monocyclic cycloalkylene groups having 3 to 10 carbon atoms, such as a 1,3-cyclobutylene group, a 1,3-cyclopentylene group, a 1,4-cyclohexylene group, and a 1,5-cyclooctylene group; polycyclic cycloalkylene groups such as a 1,4-norbornylene group, a 2,5-norbornylene group, a 1,5-admantylene group, and a 2,6-admantylene group; and the like.

Examples of the divalent aromatic hydrocarbon group having 6 to 30 carbon atoms represented by A in the general formulas (3-2) and (3-3) include arylene groups such as a phenylene group, a tolylene group, a naphthylene group, a phenanthrylene group, and an anthrylene group, and the like.

Specific examples of the repeating unit that includes an alicyclic hydrocarbon group or a derivative thereof (hereinafter may be referred to as "repeating unit (4)") include a repeating unit shown by the following general formula (4).

(4)

wherein $R^9$ represents a hydrogen atom, a methyl group, or a trifluoromethyl group, and $R^{10}$ represents an alicyclic hydrocarbon group having 4 to 20 carbon atoms or a derivative thereof.

Examples of the alicyclic hydrocarbon group having 4 to 20 carbon atoms represented by $R^{10}$ in the general formula (4) include a hydrocarbon group that includes an alicyclic ring derived from a cycloalkane such as cyclobutane, cyclopentane, cyclohexane, bicyclo[2.2.1]heptane, bicyclo[2.2.2]octane, tricyclo[5.2.1.0$^{2,6}$]decane, tetracyclo[6.2.1.1$^{3,6}$.0$^{2,7}$]dodecane, or tricycle[3.3.1.1$^{3,7}$]decane.

Examples of the derivative of the alicyclic hydrocarbon group represented by $R^{10}$ include a group obtained by substituting at least one hydrogen atom of the above alicyclic hydrocarbon group with at least one of a linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, a hydroxyl group, a cyano group, a hydroxyalkyl group having 1 to 10 carbon atoms, a carboxyl group, an oxygen atom, and the like.

The content of the repeating unit (1) in the fluorine-containing polymer (A) is preferably 5 to 50 mol %, more preferably 10 to 40 mol %, and particularly preferably 15 to 30 mol %, based on the total amount (=100 mol %) of the repeating units included in the fluorine-containing polymer (A). If the content of the repeating unit (1) is less than 5 mol %, a sufficiently high receding contact angle may not be obtained. If the content of the repeating unit (1) is more than 50 mol %, an excellent pattern shape may not be obtained due to a decrease in solubility of the fluorine-containing polymer (A) in a developer.

The content of the repeating unit (2) is preferably 5 to 95 mol %, preferably 30 to 90 mol %, and more preferably 50 to 85 mol %. This makes it possible to implement a sufficiently high receding contact angle and excellent lithographic performance.

The fluorine-containing polymer (A) may be produced by polymerizing polymerizable unsaturated monomers that correspond to the above repeating units in an appropriate solvent optionally in the presence of a chain transfer agent using a radical polymerization initiator such as a hydroperoxide, a dialkyl peroxide, a diacyl peroxide, or an azo compound, for example.

Examples of the solvent used to produce the fluorine-containing polymer (A) include alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylates such as ethyl acetate, n-butyl acetate, i-butyl acetate, and methyl propionate; ketones such as acetone, 2-butanone, 4-methyl-2-pentanone, and 2-heptanone; ethers such as tetrahydrofuran, dimethoxyethanes, and diethoxyethanes; alcohols such as methanol, ethanol, 1-propanol, 2-propanol, and 4-methyl-2-pentanol; and the like. These solvents may be used either individually or in combination.

The reaction temperature when producing the polymer (A) is preferably 40 to 150° C., and more preferably 50 to 120° C. The reaction time is preferably 1 to 48 hours, and more preferably 1 to 24 hours.

The polystyrene-reduced weight average molecular weight (Mw) of the polymer (A) determined by gel permeation chromatography (GPC) is preferably 1000 to 50,000, more preferably 1000 to 40,000, and particularly preferably 1000 to 30,000. If the Mw of the polymer (A) is less than 1000, a sufficiently high receding contact angle may not be obtained. If the Mw of the polymer (A) is more than 50,000, the developability of the resulting resist may decrease.

The ratio (Mw/Mn) of the Mw to the polystyrene-reduced number average molecular weight (Mn) of the polymer (A) determined by GPC is preferably 1 to 5, and more preferably 1 to 4.

It is preferable that the content of impurities (e.g., halogen or metal) in the polymer (A) be as low as possible. If the polymer (A) has a low impurity content, the sensitivity, the resolution, the process stability, the pattern shape, and the like of the resulting resist are further improved.

The polymer (A) may be purified by chemical purification (e.g., washing with water or liquid-liquid extraction), or a combination of chemical purification and physical purification (e.g., ultrafiltration or centrifugation), for example.

[1-3] Acid-Labile Group-Containing Polymer (B)

The acid-labile group-containing polymer (B) is not particularly limited insofar as the fluorine-containing polymer (A) advantageously exerts its effects (i.e., an increase in receding contact angle, a decrease in elution volume, and suppression of development defects), but is preferably a polymer that is insoluble or scarcely soluble in alkali, but becomes alkali-soluble due to an acid.

The expression "insoluble or scarcely soluble in alkali" means that a resist film that is formed only of the polymer (B) has a thickness equal to or more than 50% of the initial thickness when developed under alkaline development conditions employed when forming a resist pattern using a resist film that is formed of a radiation-sensitive composition that includes the polymer (B).

Examples of the polymer (B) include a polymer that includes an alicyclic skeleton such as a norbornane ring in the main chain and is obtained by polymerizing a norbornene derivative or the like, a polymer that includes a norbornane ring and a maleic anhydride derivative in the main chain and is obtained by copolymerizing a norbornene derivative and maleic anhydride, a polymer that includes a norbornane ring and a (meth)acrylic skeleton in the main chain and is obtained by copolymerizing a norbornene derivative and a (meth) acrylic compound, a polymer that includes a norbornane ring, a maleic anhydride derivative, and a (meth)acrylic skeleton in the main chain and is obtained by copolymerizing a norbornene derivative, maleic anhydride, and a (meth)acrylic compound, a polymer that includes a (meth)acrylic skeleton in the main chain and is obtained by copolymerizing (meth) acrylic compounds, and the like.

The polymer (B) is preferably a polymer that includes a (meth)acrylic skeleton in the main chain, and particularly preferably a polymer that includes at least one repeating unit (3) that includes a lactone skeleton. It is preferable that the polymer (B) include at least one repeating unit (2) in addition to the repeating unit (3).

The content of each repeating unit based on the total amount (100 mol %) of the repeating units included in the polymer (B) is preferably as follows.

The content of the repeating unit (3) that includes a lactone skeleton is preferably 5 to 85 mol %, more preferably 10 to 70 mol %, and particularly preferably 15 to 60 mol %. If the content of the repeating unit (3) is less than 5 mol %, the developability and the exposure latitude may deteriorate. If the content of the repeating unit (3) is more than 85 mol %, the solubility of the polymer (B) in a solvent and the resolution may deteriorate.

The content of the repeating unit (2) is preferably 10 to 70 mol %, more preferably 15 to 60 mol %, and particularly preferably 20 to 50 mol %. If the content of the repeating unit (2) is less than 10 mol %, the resolution of the resulting resist may decrease. If the content of the repeating unit (2) is more than 70 mol %, the exposure latitude may deteriorate.

The polymer (B) may be produced by polymerizing polymerizable unsaturated monomers that correspond to the above repeating units in an appropriate solvent optionally in the presence of a chain transfer agent using a radical polymerization initiator such as a hydroperoxide, a dialkyl peroxide, a diacyl peroxide, or an azo compound.

Examples of the solvent used to produce the polymer (B) include alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylates such as ethyl acetate, n-butyl acetate, i-butyl acetate, and methyl propionate; ketones such as acetone, 2-butanone, 4-methyl-2-pentanone, and 2-heptanone; ethers such as tetrahydrofuran, dimethoxyethanes, and diethoxyethanes; and the like. These solvents may be used either individually or in combination.

The reaction temperature when producing the polymer (B) is preferably 40 to 150° C., and more preferably 50 to 120° C. The reaction time is preferably 1 to 48 hours, and more preferably 1 to 24 hours.

The Mw of the polymer (B) determined by GPC is preferably 1000 to 100,000, more preferably 1000 to 30,000, and particularly preferably 1000 to 20,000. If the Mw of the polymer (B) is less than 1000, the heat resistance of the resulting resist may decrease. If the Mw of the polymer (B) is more than 100,000, the developability of the resulting resist may decrease. The ratio (Mw/Mn) of the Mw to the Mn of the polymer (B) determined by GPC is preferably 1 to 5, and more preferably 1 to 3.

The content (solid content) of low-molecular-weight components derived from the monomers used to produce the polymer (B) is preferably 0.1 mass % or less, more preferably 0.07 mass % or less, and particularly preferably 0.05 mass % or less, based on 100 mass % of the polymer (B). If the content of low-molecular-weight components is 0.1 mass % or less, the elution volume upon contact with an immersion liquid (e.g., water) during liquid immersion lithography can be reduced. Moreover, it is possible to prevent production of foreign substances during storage of the resist, prevent uneven resist application, and sufficiently suppress of occurrence defects when forming a resist pattern.

Examples of low-molecular-weight components derived from the monomers include components (e.g., monomer, dimer, trimer, and oligomer) having an Mw of 500 or less. Components having an Mw of 500 or less may be removed by chemical purification (e.g., washing with water or liquid-liquid extraction), or a combination of chemical purification and physical purification (e.g., ultrafiltration or centrifugation), for example. The content of low-molecular-weight components may be determined by high-performance liquid chromatography (HPLC).

It is preferable that the impurity (e.g., halogen or metal) content in the polymer (B) be as low as possible. If the polymer (B) has a low impurity content, the sensitivity, the resolution, the process stability, the pattern shape, and the like of the resulting resist are further improved.

The polymer (B) may be purified by chemical purification (e.g., washing with water or liquid-liquid extraction) or a combination of chemical purification and physical purification (e.g., ultrafiltration or centrifugation), for example.

The radiation-sensitive composition may include only one type of polymer (B), or may include two or more of types of polymer (B).

[1-4] Solvent (D)

The radiation-sensitive composition according to one embodiment of the invention includes the solvent (hereinafter may be referred to as "solvent (D)").

The radiation-sensitive composition is normally used as a composition solution by dissolving the components in a solvent so that the total solid content is normally 1 to 50 mass %, and preferably 1 to 25 mass %, and filtering the solution using a filter having a pore size of about 0.2 μm, for example.

Examples of the solvent (D) include linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, ethyl 2-hydroxy-2-methyl propionate, ethoxyethyl acetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethyl acetate, n-propyl acetate, n-butyl acetate, methyl acetoacetate, ethyl acetoacetate, methyl pyruvate, ethyl pyruvate, N-methylpyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and the like.

Among these, linear or branched ketones, cyclic ketones, propylene glycol monoalkyl ether acetates, alkyl 2-hydroxypropionates, alkyl 3-alkoxypropionates, γ-butyrolactone, and the like are preferable. These solvents may be used either individually or in combination.

[1-5] Photoacid Generator (C)

The radiation-sensitive composition according to one embodiment of the invention preferably includes (C) a photoacid generator in addition to the fluorine-containing polymer (A), the acid-labile group-containing polymer (B), and the solvent (D).

The photoacid generator (C) (hereinafter may be referred to as "acid generator (C)") produces an acid upon exposure. The acid-dissociable group of the repeating unit (2) included in the polymer component (polymers (A) and (B)) dissociates (i.e., the protecting group is eliminated) due to the acid produced by the photoacid generator (C), so that the exposed area of the resist film becomes readily soluble in an alkaline developer to obtain a positive-tone resist pattern.

The acid generator (C) preferably includes a compound shown by the following general formula (5).

wherein $R^{11}$ represents a hydrogen atom, a fluorine atom, a hydroxyl group, a linear or branched alkyl group having 1 to 10 carbon atoms, a linear or branched alkoxy group having 1 to 10 carbon atoms, or a linear or branched alkoxycarbonyl group having 2 to 11 carbon atoms.

$R^{12}$ represents a linear or branched alkyl group having 1 to 10 carbon atoms, a linear or branched alkoxy group having 1 to 10 carbon atoms, or a linear, branched, or cyclic alkanesulfonyl group having 1 to 10 carbon atoms. $R^{13}$ individually represent a linear or branched alkyl group having 1 to 10 carbon atoms, a substituted or unsubstituted phenyl group, or a substituted or unsubstituted naphthyl group, or bond to form a substituted or unsubstituted divalent group having 2 to 10 carbon atoms.

k is an integer from 0 to 2, $Z^-$ represents an anion shown by the following general formula (6), and r is an integer from 0 to 10.

$$R^{14}C_qF_{2q}SO_3^- \quad (6)$$

wherein $R^{14}$ represents a fluorine atom or a substituted or unsubstituted hydrocarbon group having 1 to 12 carbon atoms, and q is an integer from 1 to 10.

Examples of the linear or the branched alkyl group having 1 to 10 carbon atoms represented by $R^{11}$, $R^{12}$, and $R^{13}$ in the general formula (5) include a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group, and the like. Among these, a methyl group, an ethyl group, an n-butyl group, a t-butyl group, and the like are preferable.

Examples of the linear or branched alkoxy group having 1 to 10 carbon atoms represented by $R^{11}$ and $R^{12}$ include a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group, and the like. Among these, a methoxy group, an ethoxy group, an n-propoxy group, an n-butoxy group, and the like are preferable.

Examples of the linear or branched alkoxycarbonyl group having 2 to 11 carbon atoms represented by $R^{11}$ include a methoxycarbonyl group, an ethoxycarbonyl group, an n-propoxycarbonyl group, an i-propoxycarbonyl group, an n-butoxycarbonyl group, a 2-methylpropoxycarbonyl group, an 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group, and the like. Among these, a methoxycarbonyl group, an ethoxycarbonyl group, an n-butoxycarbonyl group, and the like are preferable.

Examples of the linear, branched, or cyclic alkanesulfonyl group having 1 to 10 carbon atoms represented by $R^{12}$ include a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group, and the like. Among these, a methanesylfonyl group, an ethanesulfonyl group, an n-propanesulfonyl group, an n-butanesulfonyl group, a cyclopentansulfonyl group, a cyclohexanesulfonyl group, and the like are preferable.

r in the general formula (5) is preferably an integer from 0 to 2.

Examples of the substituted or unsubstituted phenyl group represented by $R^{13}$ in the general formula (5) include a phenyl group, a phenyl group substituted with a linear, branched, or cyclic alkyl group having 1 to 10 carbon atoms, such as an o-tolyl group, an m-tolyl group, a p-tolyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 4-ethylphenyl group, a 4-t-butylphenyl group, 4-cyclohexylphenyl group, or a 4-fluorophenyl group; a group obtained by substituting the phenyl group or the alkyl-substituted phenyl group with at least one group such as a hydroxyl group, a carboxyl group, a cyano group, a nitro group, an alkoxy group, an alkoxyalkyl group, an alkoxycarbonyl group, or an alkoxycarbonyloxy group; and the like.

Examples of the alkoxy group as a substituent for the phenyl group or the alkyl-substituted phenyl group include linear, branched, or cyclic alkoxy groups having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group, and a cyclohexyloxy group, and the like.

Examples of the alkoxyalkyl group include linear, branched, or cyclic alkoxyalkyl groups having 2 to 21 carbon atoms, such as a methoxymethyl group, an ethoxymethyl group, a 1-methoxyethyl group, a 2-methoxyethyl group, a 1-ethoxyethyl group, and a 2-ethoxyethyl group, and the like.

Examples of the alkoxycarbonyl group include linear, branched, or cyclic alkoxycarbonyl groups having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group, and a cyclohexyloxycarbonyl group, and the like.

Examples of the alkoxycarbonyloxy group include linear, branched, or cyclic alkoxycarbonyloxy groups having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyl group, and a cyclohexyloxycarbonyl group, and the like.

Among the above substituted or unsubstituted phenyl groups, a phenyl group, a 4-cyclohexylphenyl group, a 4-t-butylphenyl group, a 4-methoxyphenyl group, a 4-t-butoxyphenyl group, and the like are preferable.

Examples of the substituted or unsubstituted naphthyl group represented by $R^{13}$ in the general formula (5) include naphthyl groups substituted or unsubstituted with a linear, branched, or cyclic alkyl group having 1 to 10 carbon atoms, such as a 1-naphthyl group, a 2-methyl-1-naphthyl group, a 3-methyl-1-naphthyl group, a 4-methyl-1-naphthyl group, a 4-methyl-1-naphthyl group, a 5-methyl-1-naphthyl group, a 6-methyl-1-naphthyl group, a 7-methyl-1-naphthyl group, a 8-methyl-1-naphthyl group, a 2,3-dimethyl-1-naphthyl group, a 2,4-dimethyl-1-naphthyl group, a 2,5-dimethyl-1-naphthyl group, a 2,6-dimethyl-1-naphthyl group, a 2,7-dimethyl-1-naphthyl group, a 2,8-dimethyl-1-naphthyl group, a 3,4-dimethyl-1-naphthyl group, a 3,5-dimethyl-1-naphthyl group, a 3,6-dimethyl-1-naphthyl group, a 3,7-dimethyl-1-naphthyl group, a 3,8-dimethyl-1-naphthyl group, a 4,5-dimethyl-1-naphthyl group, a 5,8-dimethyl-1-naphthyl group, a 4-ethyl-1-naphthyl group, a 2-naphthyl group, a 1-methyl-2-naphthyl group, a 3-methyl-2-naphthyl group, and a 4-methyl-2-naphthyl group; a group obtained by substituting a naphthyl group or the alkyl-substituted naphthyl group with at least one group such as a hydroxyl group, a carboxyl group, a cyano group, a nitro group, an alkoxyl group, an alkoxyalkyl group, an alkoxycarbonyl group, or an alkoxycarbonyloxy group; and the like.

Examples of the alkoxy group, the alkoxyalkyl group, the alkoxycarbonyl group, and the alkoxycarbonyloxy group as a substituent include the groups mentioned above in connection with a phenyl group and the alkyl-substituted phenyl group.

Among the above substituted or unsubstituted naphthyl groups, a 1-naphthyl group, a 1-(4-methoxynaphthyl) group, a 1-(4-ethoxynaphthyl) group, a 1-(4-n-propoxynaphthyl) group, a 1-(4-n-butoxynaphthyl) group, a 2-(7-methoxynaphthyl) group, a 2-(7-ethoxynaphthyl) group, a 2-(7-n-propoxynaphthyl) group, a 2-(7-n-butoxynaphthyl) group, and the like are preferable.

The divalent group having 2 to 10 carbon atoms formed by two $R^{13}$ is preferably a group that forms a five- or six-membered ring (particularly preferably a five-membered ring (i.e., tetrahydrothiophene ring)) together with the sulfur atom in the general formula (5).

Examples of a substituent for the divalent group include the groups (e.g., hydroxyl group, carboxyl group, cyano group, nitro group, alkoxyl group, alkoxyalkyl group, alkoxycarbonyl group, and alkoxycarbonyloxy group) mentioned above in connection with a phenyl group and the alkyl-substituted phenyl group.

It is preferable that $R^{13}$ in the general formula (5) be a methyl group, an ethyl group, a phenyl group, a 4-methoxyphenyl group, a 1-naphthyl group, or the like, or bond to form a divalent group that forms a tetrahydrothiophene ring structure together with the sulfur atom.

The $C_qF_{2q}^-$ group in the anion (general formula (6)) represented by $Z^-$ in the general formula (5) is a linear or branched perfluoroalkylene group having q carbon atoms. q in the general formula (6) is preferably 1, 2, 4, or 8.

The substituted or unsubstituted hydrocarbon group having 1 to 12 carbon atoms represented by $R^{14}$ is preferably an alkyl group having 1 to 12 carbon atoms, a cycloalkyl group, or a bridged alicyclic hydrocarbon group.

Specific examples of the substituted or unsubstituted hydrocarbon group having 1 to 12 carbon atoms represented by $R^{14}$ include a methyl group, an ethyl group, an n-propyl group, an i-propyl group, an n-butyl group, a 2-methylpropyl group, a 1-methylpropyl group, a t-butyl group, an n-pentyl group, an neopentyl group, an n-hexyl group, a cyclohexyl group, an n-heptyl group, an n-octyl group, a 2-ethylhexyl group, an n-nonyl group, an n-decyl group, a norbornyl group, a norbornylmethyl group, a hydroxynorbornyl group, an adamantyl group, and the like.

Specific examples of a preferable compound shown by the general formula (5) include triphenylsulfonium trifluoromethanesulfonate, tri-tert-butylphenylsulfonium trifluoromethanesulfonate, 4-cyclohexylphenyl-diphenylsulfonium trifluoromethanesulfonate, 4-methanesulfonylphenyl-diphenylsulfonium trifluoromethanesulfonate, 1-(3,5-dimethyl 4-hydroxyphenyl)tetrahydrothiophenium trifluoromethanesulfonate, 1-(4-n-butoxynaphthyl)tetrahydrothiophenium trifluoromethanesulfonate, triphenylsulfonium perfluoro-n-butanesulfonate, tri-tert-butylphenylsulfonium perfluoro-n-butanesulfonate, 4-cyclohexylphenyl-diphenylsulfonium perfluoro-n-butanesulfonate, 4-methanesulfonylphenyl-diphenylsulfonium perfluoro-n-butanesulfonate, 1-(3,5-dimethyl-4-hydroxyphenyl)tetrahydrothiophenium perfluoro-n-butanesulfonate, 1-(4-n-butoxynaphthyl)tetrahydrothiophenium perfluoro-n-butanesulfonate, triphenylsulfonium perfluoro-n-octanesulfonate, tri-tert-butylphenylsulfonium perfluoro-n-octanesulfonate, 4-cyclohexylphenyl-diphenylsulfonium perfluoro-n-octanesulfonate, 4-methanesulfonylphenyl-diphenylsulfonium perfluoro-n-octanesulfonate, 1-(3,5-dimethyl-4-hydroxyphenyl)tetrahydrothiophenium perfluoro-n-octanesulfonate, 1-(4-n-butoxynaphthyl)tetrahydrothiophenium perfluoro-n-octanesulfonate, triphenylsulfonium 2-(bicyclo[2.2.1]hept-2'-yl)-1,1,2,2-tetrafluoroethanesulfonate, tri-tert-butylphenylsulfonium 2-(bicyclo[2.2.1]hept-2'-yl)-1,1,2,2-tetrafluoroethanesulfonate, 4-cyclohexylphenyldiphenylsulfonium 2-(bicyclo[2.2.1]hept-2'-yl)-1,1,2,2-tetrafluoroethane sulfonate, 4-methanesulfonylphenyldiphenylsulfonim 2-(bicyclo[2.2.1]hept-2'-yl)-1,1,2,2-tetrafluoroethanesulfonate, 1-(3,5-dimethyl-4-hydroxyphenyl)tetrahydrothiophenium 2-(bicyclo[2.2.1]hept-2'-yl)-1,1,2,2-tetrafluoroethanesulfonate, 1-(4-n-butoxynaphthyl)tetrahydrothiophenium 2-(bicyclo[2.2.1]hept-2'-yl)-1,1,2,2-tetrafluoroethanesulfonate, triphenylsulfonium 2-(bicyclo[2.2.1]hept-2'-yl)-1,1-difluoroethanesulfonate, tri-tert-butylphenylsulfonium 2-(bicyclo[2.2.1]hept-2'-yl)-1,1-difluoroethanesulfonate, 4-cyclohexylphenyldiphenylsulfonium 2-(bicyclo[2.2.1]hept-2'-yl)-1,1-difluoroethane sulfonate, 4-methanesulfonylphenyldiphenylsulfonium 2-(bicyclo[2.2.1]hept-2'-yl)-1,1-difluoroethanesulfonate, 1-(3,5-dimethyl-4-hydroxyphenyl)tetrahydrothiophenium 2-(bicyclo[2.2.1]hept-2'-yl)-1,1-difluoroethanesulfonate, 1-(4-n-butoxynaphthyl)tetrahydrothiophenium 2-(bicyclo[2.2.1]hept-2'-yl)-1,1-difluoroethanesulfonate, and the like.

These acid generators (C) may be used either individually or in combination.

[1-6] Nitrogen-Containing Compound (E)

The radiation-sensitive composition according to one embodiment of the invention may further include a nitrogen-containing compound (hereinafter may be referred to as "nitrogen-containing compound (E)") as an additive.

The nitrogen-containing compound (E) controls diffusion of an acid generated from the acid generator upon exposure within the resist film to suppress undesired chemical reactions in the unexposed area. The storage stability of the resulting radiation-sensitive composition is improved by adding the acid diffusion controller. Moreover, the acid diffusion controller further improves the resolution of the resulting resist, and suppresses a change in line width of the resist pattern due to a variation in post-exposure delay (PED). Specifically, a composition that exhibits excellent process stability can be obtained.

Examples of the nitrogen-containing compound (E) include tertiary amine compounds, other amine compounds, amide group-containing compounds, urea compounds, nitrogen-containing heterocyclic compounds, and the like.

These nitrogen-containing compounds (E) may be used either individually or in combination.

The nitrogen-containing compound (E) is preferably used in an amount of 15 parts by mass or less, more preferably 10 parts by mass or less, and particularly preferably 5 parts by mass or less, based on 100 parts by mass of the polymers (A) and (B). If the amount of the nitrogen-containing compound (E) is more than 15 parts by mass, the sensitivity of the resulting resist may decrease. If the amount of the acid diffusion controller is less than 0.001 parts by mass, the pattern shape or the dimensional accuracy of the resulting resist may decrease depending on the processing conditions.

[1-7] Other Additives

The radiation-sensitive composition according to one embodiment of the invention may optionally further include other additives such as an aliphatic additive, a surfactant, and a sensitizer.

The alicyclic additive further improves the dry etching resistance, the pattern shape, adhesion to a substrate, and the like.

Examples of the alicyclic additive include adamantane derivatives such as 1-adamantanecarboxylic acid, 2-adamantanone, t-butyl-1-adamantanecarboxylate, t-butoxycarbonylmethyl 1-adamantanecarboxylate, α-butyrolactone 1-adamantanecarboxylate, di-t-butyl 1,3-adamantanedicarboxylate, t-butyl 1-adamantaneacetate, t-butoxycarbonylmethyl 1-adamantaneacetate, di-t-butyl 1,3-adamantanediacetate, and 2,5-dimethyl-2,5-di(adamantylcarbonyloxy)hexane; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; alkyl carboxylates such as dimethyl adipate, diethyl adipate, dipropyl adipate, di-n-butyl adipate, and di-t-butyl adipate; 3-[2-hydroxy-2,2-bis(trifluoromethyl)ethyl]tetracyclo[4.4.0.1$^{2,5}$.1$^{7,10}$]dodecane; and the like. These alicyclic additives may be used either individually or in combination.

The surfactant improves applicability, striation, developability, and the like.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate, commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination.

The sensitizer absorbs the energy of radiation, and transmits the energy to the acid generator (C), so that the amount of acid generated by the acid generator (B) increases. The sensitizer improves the apparent sensitivity of the radiation-sensitive composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

A dye or a pigment visualizes the latent image in the exposed area to reduce the effects of halation during exposure. An adhesion improver improves adhesion to a substrate. Examples of other additives include an alkali-soluble resin, a low-molecular-weight alkali-solubility controller that includes an acid-dissociable protecting group, a halation inhibitor, a preservation stabilizer, an antifoaming agent, and the like.

[1-8] Resist Pattern-Forming Method

The radiation-sensitive composition according to one embodiment of the invention is useful as a chemically-amplified resist. When using the radiation-sensitive composition as a chemically-amplified resist, the acid-dissociable group included in the polymer component dissociates due to an acid generated by the acid generator upon exposure so that a carboxyl group is produced. As a result, the solubility of the exposed area of the resist in an alkaline developer increases. Therefore, the exposed area is dissolved (removed) in an alkaline developer to obtain a positive-tone resist pattern.

When forming a resist pattern using the radiation-sensitive composition according to one embodiment of the invention, the composition solution is applied to a substrate (e.g., silicon wafer or aluminum-coated wafer) by an appropriate application method (e.g., rotational coating, cast coating, or roll coating) to form a resist film. The resist film is optionally pre-baked (PB), and exposed to form a given resist pattern.

As radiation used for exposure, visible rays, ultraviolet rays, deep ultraviolet rays, X-rays, electron beams, or the like are appropriately selected depending on the type of acid generator. It is preferable to use deep ultraviolet rays such as ArF excimer laser light (wavelength: 193 nm) or KrF excimer laser light (wavelength: 248 nm). It is particularly preferable to use ArF excimer laser light (wavelength: 193 nm).

The exposure conditions (e.g., dose) are appropriately selected depending on the composition of the radiation-sensitive composition, the type of additive, and the like. It is preferable to perform post-exposure bake (PEB). The acid-dissociable group included in the polymer component smoothly dissociates due to PEB. The PEB temperature is determined depending on the composition of the radiation-sensitive composition, but is preferably 30 to 200° C., and more preferably 50 to 170° C.

In order to bring out the potential of the radiation-sensitive composition to a maximum extent, an organic or inorganic antireflective film may be formed on a substrate, as disclosed in Japanese Examined Patent Publication (KOKOKU) No. 6-12452 (Japanese Patent Application Publication (KOKAI) No. 59-93448), for example. A protective film may be formed on the resist film so that the resist film is not affected by basic impurities and the like contained in the environmental atmosphere, as disclosed in Japanese Patent Application Publication (KOKAI) No. 5-188598, for example. In order to prevent outflow of the acid generator and the like from the resist film during liquid immersion lithography, a liquid immersion lithography protective film may be formed on the resist film, as disclosed in Japanese Patent Application Publication (KOKAI) No. 2005-352384, for example. These technologies may be used in combination.

The exposed resist film is developed using a developer to form a given resist pattern.

As the developer, it is preferable to use an alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water. The concentration of the alkaline aqueous solution is normally 10 mass % or less. If the concentration of the alkaline aqueous solution is more than 10 mass %, the unexposed area may also be dissolved in the developer.

An organic solvent may be added to the alkaline aqueous solution (developer), for example. Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methanol, ethanol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide; and the like. These organic solvents may be used either individually or in combination.

The organic solvent is preferably used in an amount of 100 vol % or less based on the amount of the alkaline aqueous solution. If the amount of the organic solvent is more than 100 vol %, the exposed area may remain undeveloped due to a decrease in developability. An appropriate amount of surfactant or the like may also be added to the alkaline aqueous solution (developer). After development using the alkaline aqueous solution (developer), the resist film is normally washed with water, and dried.

[2] Novel Compound

A novel compound according to one embodiment of the invention is described below. The novel compound according to one embodiment of the invention forms the repeating unit (1) that forms the fluorine-containing polymer (A) included in the radiation-sensitive composition according to one embodiment of the invention. Specifically, the novel compound (monomer) according to one embodiment of the invention is shown by the general formula (1).

[2-1] Method of Producing Novel Compound

The novel compound according to one embodiment of the invention that includes the fluorine-containing polymer may be produced by reacting a desired fluoroalcohol and a diester compound in an appropriate solvent in the presence of an amine, for example.

Examples of the amine include, but are not limited to, triethylamine, 1,4-diazabicyclo[2.2.2]octane, pyridine, and the like.

The reaction temperature when synthesizing the novel compound is preferably −15 to 100° C., more preferably 0 to 80° C., and particularly preferably 20 to 70° C. The monomer (A) may be synthesized in air, but is preferably synthesized in an inert gas atmosphere (e.g., nitrogen or argon).

The novel compound may be purified by distillation or column chromatography, for example.

The novel compound according to one embodiment of the invention may suitably be used as a monomer component that forms the polymer (fluorine-containing polymer (A)) included in the radiation-sensitive composition according to one embodiment of the invention.

[3] Fluorine-Containing Polymer

A fluorine-containing polymer according to one embodiment of the invention is described below. The fluorine-containing polymer according to one embodiment of the invention is formed in the same manner as the fluorine-containing polymer (A) included in the radiation-sensitive composition according to one embodiment of the invention. Specifically, the fluorine-containing polymer according to one embodiment of the invention is a novel polymer including the repeating unit (1) derived from the compound shown by the general formula (1).

The fluorine-containing polymer may suitably be used for the radiation-sensitive composition according to one embodiment of the invention. The fluorine-containing polymer may further include the repeating units (2) to (4) mentioned above in connection with the fluorine-containing polymer (A). The description given above in connection with the fluorine-containing polymer (A) applies to a preferable content of each repeating unit and the like.

EXAMPLES

The embodiment of the invention is further described below by way of examples. Note that the invention is not limited to the following examples. In the examples, the unit "parts" refers to "parts by mass" unless otherwise indicated. The following measurement/evaluation methods were used in each synthesis example.

(1) Mw and Mn

The Mw and the Mn of each polymer were determined by gel permeation chromatography (GPC) (standard: monodispersed polystyrene) using a GPC column manufactured by Tosoh Corp. (G2000HXL×2, G3000HXL×1, G4000HXL×1) (flow rate: 1.0 ml/min, column temperature: 40° C., eluant: tetrahydrofuran). The dispersity (Mw/Mn) was calculated from the measurement results.

(2) $^{13}$C-NMR Analysis

Each polymer was subjected to $^{13}$C-NMR analysis using "JNM-EX270" (manufactured by JEOL Ltd.).
(1) Synthesis of Monomer (a-3)

A three-necked flask (200 ml) equipped with a reflux cooling tube and a dropping funnel was charged with 17.65 g (60 mmol) of a compound (a-1) shown by the following formula (a-1), 31.52 g (15 mmol) of NEt, 1.83 g (15 mmol) of dimethylaminopyridine (DMAP), and 80 ml of tetrahydrofuran (THF). THF was refluxed at 70° C. using an oil bath.

A solution prepared by dissolving 19.64 g (90 mmol) of a compound (a-2) shown by the following formula (a-2) in 20 ml of THF was added dropwise to the mixture over five minutes. The reaction was tracked by thin-layer chromatography (TLC), and terminated when the compound (a-1) had disappeared. The mixture was then allowed to cool to room temperature.

After the addition of 40 ml of water and 75 ml of ethyl acetate, the organic layer was removed by a separation operation. The organic layer was concentrated using a rotary evaporator, and subjected to silica gel column chromatography ("Wakogel C-300" manufactured by Wako Pure Chemical Industries, Ltd.) using hexane/ethyl acetate (=2/1) to isolate the target compound (a-3) shown by the following formula (a-3) (colorless liquid) (yield: 80%).

The $^{1}$H-NMR analysis results ($^{1}$H-NMR (400 MHz, CDCl$_3$), δ (ppm): 6.10 (d, 1H), 5.47 (d, 1H), 5.22-5.11 (m, 1H), 2.70-2.90 (m, 2H), 1.92 (s, 3H), 1.50 (s, 9H), 1.35 (d, 3H)) indicate that the target compound was obtained. The $^{1}$H-NMR analysis was conducted in the same manner as the $^{13}$C-NMR analysis.

(a-1)

(a-2)

(a-3)

(2-1) Synthesis of Fluorine-Containing Polymer (A-1)

The following monomers (M-1) to (M-7) were used to synthesize fluorine-containing polymers (A-1) to (A-6). The monomer (M-2) is the compound (a-3) synthesized as described above.

(M-1)

(M-2)

(M-3)

(M-4)

(M-5)

(M-6)

(M-7)

70 mol % of the monomer (M-1), 30 mol % of the monomer (M-2), and an initiator (dimethyl-2,2'-azobisisobutyrate (MAIB)) were dissolved in 50 g of methyl ethyl ketone to prepare a monomer solution. The total amount of the monomers was 50 g. Table 1 shows the combination and the amounts (mol %) of monomers. Note that the amount (mol %) of each monomer is based on the total amount of the monomers, and the amount (mol %) of the initiator is based on the total amount of the monomers and the initiator.

A 500 ml three-necked flask equipped with a thermometer and a dropping funnel was charged with 50 g of methyl ethyl ketone, and purged with nitrogen for 30 minutes. The inside of the flask was heated to 80° C. with stirring using a magnetic stirrer.

The monomer solution was added dropwise to the flask over three hours using the dropping funnel. After the addition, the mixture was aged for three hours, and cooled to 30° C. or less to obtain a copolymer solution.

After washing the reaction (copolymer) solution with a methanol solution in a slurry state, it was collected by filtration, and dried at 50° C. for 17 hours to obtain a white powdery copolymer. The content (mass %) of each polymer was measured by gas chromatography, and the Mw, the Mw/Mn ratio (molecular weight dispersibility), and the yield (mass %) of each polymer, and the proportion (mol %) of each repeating unit included in each polymer were measured. The results are shown in Table 2.

TABLE 1

| | Polymer (A) | Monomer 1 | Amount (mol %) | Monomer 2 | Amount (mol %) | Initiator (mol %) |
|---|---|---|---|---|---|---|
| Polymerization Example 1 | A-1 | M-1 | 70 | M-2 | 30 | 8 |
| Polymerization Example 2 | A-2 | M-1 | 85 | M-2 | 15 | 8 |
| Polymerization Example 3 | A-3 | M-3 | 70 | M-2 | 30 | 8 |
| Polymerization Example 4 | A-4 | M-3 | 85 | M-2 | 15 | 8 |
| Polymerization Example 5 | A-5 | M-7 | 70 | M-2 | 30 | 8 |
| Polymerization Example 6 | A-6 | M-7 | 85 | M-2 | 15 | 8 |

TABLE 2

| | Polymer (A) | Yield (%) | Monomer 1 (mol %) | Monomer 2 (mol %) | Mw | Mw/Mn |
|---|---|---|---|---|---|---|
| Polymerization Example 1 | A-1 | 66.3 | 71.1 | 28.9 | 5600 | 1.22 |
| Polymerization Example 2 | A-2 | 64.5 | 84.8 | 15.2 | 5900 | 1.35 |
| Polymerization Example 3 | A-3 | 64.2 | 70.2 | 29.8 | 7000 | 1.71 |
| Polymerization Example 4 | A-4 | 65.5 | 84.8 | 15.2 | 3900 | 1.45 |
| Polymerization Example 5 | A-5 | 51.3 | 70.3 | 29.7 | 5900 | 1.9 |
| Polymerization Example 6 | A-6 | 50.2 | 84.7 | 15.3 | 7800 | 1.31 |

(2-2) Synthesis of Fluorine-Containing Polymers (A-2) to (A-6)

Fluorine-containing polymers (A-2) to (A-6) were synthesized in the same manner as the fluorine-containing polymer (A-1), except for changing the combination and the amounts (mol %) of monomers as shown in Table 1. The Mw, the Mw/Mn ratio (molecular weight dispersity), and the yield (mass %) of each polymer, and the proportion of each repeating unit included in each polymer were measured. The results are shown in Table 2.

(3-1) Synthesis of Acid-Labile Group-Containing Polymer (B-1)

10.6 g (25 mol %) of the monomer (M-1), 13.6 g (25 mol %) of the monomer (M-5), and 25.8 g (50 mol %) of the monomer (M-6) were dissolved in 100 g of 2-butanone. 3.8 g of dimethyl 2,2'-azobis(2-methylpropionate) was added to the mixture to prepare a monomer solution.

A three-necked flask (500 ml) charged with 50 g of 2-butanone was purged with nitrogen for 30 minutes, and then heated to 80° C. with stirring. The monomer solution was added dropwise to the flask over three hours using a dropping funnel. The monomers were polymerized for six hours from the start of addition of the monomer solution.

The polymer solution was cooled with water to 30° C. or less, and poured into 2000 g of methanol. A white powdery precipitate was collected by filtration. The white powder thus collected was washed twice with 400 g of methanol in a slurry state, collected by filtration, and dried at 50° C. for 17 hours to obtain a white powdery polymer (38 g, yield: 76%).

The polymer (copolymer) had an Mw of 6800 and an Mw/Mn ratio of 1.70. The ratio of repeating units derived from the monomers (M-1), (M-5), and (M-6) determined by $^{13}$C-NMR analysis was 24.8:24.3:50.9 (mol %). This polymer is referred to as "acid-labile group-containing polymer (B-1)". The content of low-molecular-weight components derived from the monomers in the polymer was 0.03 mass %.

(3-2) Synthesis of Acid-Labile Group-Containing Polymer (B-2)

21.5 g (50 mol %) of the monomer (M-4) and 28.5 g (50 mol %) of the monomer (M-6) were dissolved in 100 g of 2-butanone. 2.1 g of dimethyl 2,2'-azobis(2-methylpropionate) was added to the mixture to prepare a monomer solution. A three-necked flask (500 ml) charged with 50 g of 2-butanone was purged with nitrogen for 30 minutes, and then heated to 80° C. with stirring. The monomer solution was added dropwise to the flask over three hours using a dropping funnel. The monomers were polymerized for six hours from the start of addition of the monomer solution.

The polymer solution was cooled with water to 30° C. or less, and poured into 2000 g of methanol. A white powdery precipitate was collected by filtration. The white powder thus collected was washed twice with 400 g of methanol in a slurry state, collected by filtration, and dried at 50° C. for 17 hours to obtain a white powdery polymer (38 g, yield: 75%).

The polymer (copolymer) had an Mw of 7200 and an Mw/Mn ratio of 1.65. The ratio of repeating units derived from the monomers (M-4) and (M-6) determined by $^{13}$C-NMR analysis was 50.2:49.8 (mol %). This polymer is referred to as "acid-labile group-containing polymer (B-2)". The content of low-molecular-weight components derived from the monomers in the polymer was 0.03 mass %.

(4-1) Example 1

Production of Radiation-Sensitive Composition

A radiation-sensitive composition of Example 1 was prepared by mixing 1 part of the fluorine-containing polymer (A-1), 100 parts of the acid-labile group-containing polymer (B-1), 7.5 parts of an acid generator (C-1), 0.65 parts of a nitrogen-containing compound (E-1), 1500 parts of a solvent (D-1), 650 parts of a solvent (D-2), and 30 parts of a solvent (D-3). Table 3 shows the amount of each component. The following acid generator, nitrogen-containing compound, and solvent were used in the examples and comparative examples.

<Acid Generator (C)>
(C-1): compound shown by the following formula (C-1)
(C-2): compound shown by the following formula (C-2)

(C-1)

(C2)

<Solvent (E)>
(D-1): propylene glycol monomethyl ether acetate (compound shown by the following formula (D-1))
(D-2): cyclohexanone (compound shown by the following formula (D-2))
(D-3): γ-butyrolactone (compound shown by the following formula (D-3))

(D-1)

(D-2)

(D-3)

<Nitrogen-Containing Compound (E)>
(E-1): N-t-Butoxycarbonyl-4-hydroxypiperidine (compound shown by the following formula (E-1))

(E-1)

(4-2) Examples 2 to 12

A radiation-sensitive composition was produced in the same manner as in Example 1, except for changing the fluorine-containing polymer, the acid-labile group-containing polymer, and the acid generator as shown in Table 3.

(4-3) Comparative Examples 1 and 2

A radiation-sensitive composition was produced in the same manner as in Example 1, except for changing the acid-labile group-containing polymer and the acid generator as shown in Table 3 without using the fluorine-containing polymer.

(5) Evaluation of Radiation-Sensitive Composition

The radiation-sensitive compositions of Examples 1 to 12 and Comparative Examples 1 and 2 were evaluated as follows. The evaluation results are shown in Table 4.

(1) Measurement of Elution Volume

Figure 1:
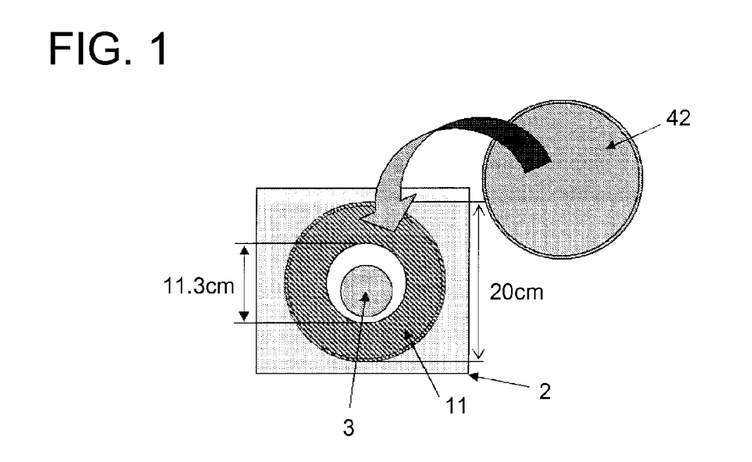
FIG. 1 is a view schematically showing a state in which an 8-inch silicon wafer is placed on a silicone rubber sheet so that leakage of ultrapure water does not occur when measuring the amount of elution from a film formed using a radiation-sensitive composition.

As shown in FIG. 1, a square (30×30 cm) silicone rubber sheet 2 (manufactured by Kureha Elastomer Co., Ltd., thickness: 1.0 mm) having a circular opening (diameter: 11.3 cm) at the center was placed at the center of an 8-inch silicon wafer 1 that was treated with hexamethyldisilazane (HMDS) (100° C., 60 sec) using a coater/developer "CLEAN TRACK ACT8" (manufactured by Tokyo Electron, Ltd.). Reference numeral 11 in FIG. 1 indicates a hexamethyldisilazane-treated layer. The center opening of the silicone rubber sheet 2 was filled with 10 ml of ultrapure water 3 using a 10 ml whole pipette.

Figure 2:
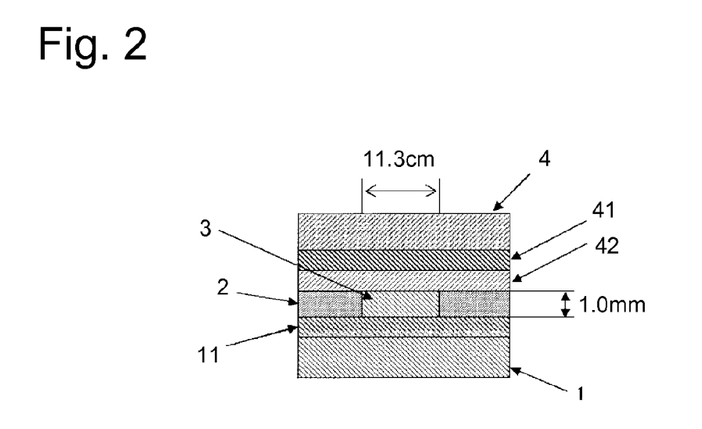
FIG. 2 is a cross-sectional view showing a state when measuring the elution volume from a film formed using a radiation-sensitive composition.

As shown in FIG. 2, an underlayer antireflective film ("ARC29A" manufactured by Bruwer Science) 41 (thickness: 77 nm) was formed using the coater/developer. The radiation-sensitive composition shown in Table 3 was spin-coated onto the underlayer antireflective film 41 using the coater/developer, and baked (115° C., 60 sec) to form a resist film 42 (thickness: 205 nm). The silicon wafer 4 was placed on the silicone rubber sheet 2 so that the surface of the resist film came in contact with the ultrapure water 3 and the ultrapure water 3 did not leak from the silicon rubber sheet 2.

After 10 seconds, the silicon wafer 4 was removed, and the ultrapure water 3 was collected using a glass syringe to obtain an analysis sample. The recovery rate of the ultrapure water 3 was 95% or more.

The peak intensity of the anion site of the acid generator included in the ultrapure water was measured under the following conditions using a liquid chromatograph mass spectrometer (LC-MS) (LC section: "SERIES 1100" manufactured by AGILENT Corp., MS section: "Mariner" manufactured by Perseptive Biosystems, Inc.). The peak intensity of an aqueous solution (1 ppb, 10 ppb, or 100 ppb) of the acid generator was measured under the following measurement conditions, and a calibration curve was drawn. The elution volume was calculated from the peak intensity using the calibration curve. Likewise, the peak intensity of an aqueous solution (1 ppb, 10 ppb, or 100 ppb) of the nitrogen-containing compound (E-1) was measured under the following measurement conditions, and a calibration curve was drawn. The elution volume of the acid diffusion controller was calculated from the peak intensity using the calibration curve. A case where the elution volume was $5.0 \times 10^{-12}$ mol/cm$^2$/sec or more was evaluated as "Bad", and a case where the elution volume was less than $5.0 \times 10^{-12}$ mol/cm$^2$/sec was evaluated as "Good".

(Measurement Conditions)
Column: CAPCELL PAK MG manufactured by Shiseido Co., Ltd.
Flow rate: 0.2 ml/min
Eluant: prepared by adding 0.1 mass % of formic acid to a water/methanol (3/7) mixture
Measurement temperature: 35° C.

(2) Measurement of Receding Contact Angle

A film of the radiation-sensitive composition was formed on a substrate (wafer). The receding contact angle was immediately measured by the following method at a temperature of 23° C. (room temperature) and a humidity of 45% under atmospheric pressure using a contact angle meter ("DSA-10" manufactured by KRUS).

Specifically, the position of the wafer stage of the contact angle meter was adjusted, and the substrate was placed on the stage. After injecting water into the needle, the position of the needle was adjusted to the initial position at which a waterdrop can be formed on the substrate. Water was discharged from the needle to form a waterdrop (25 μl) on the substrate. After removing the needle, the needle was moved downward to the initial position, and introduced into the waterdrop. The waterdrop was sucked through the needle for 90 seconds at a rate of 10 μl/min, and the contact angle formed by the liquid surface and the substrate was measured every second (90 times in total). The average value of twenty contact angle measured values (20 seconds) after the measured value became stable was calculated, and taken as the receding contact angle) (°.

(3) Sensitivity

A 12-inch silicon wafer on which an underlayer antireflective film ("ARC29A" manufactured by Bruwer Science) (thickness: 77 nm) was formed, was used as a substrate. The antireflective film was formed using the above coater/developer.

The radiation-sensitive composition was spin-coated onto the substrate using the above coater/developer, and prebaked (PB) under conditions shown in Table 4 to form a resist film having a thickness of 120 nm.

The resist film was exposed via a mask pattern using an ArF excimer laser exposure system ("NSR S306C" manufactured by Nikon Corp., NA=0.78, σ=0.93/0.69). After performing PEB under conditions shown in Table 4, the resist film was developed at 23° C. for 30 seconds using a 2.38 mass % tetramethylammonium hydroxide aqueous solution, washed with water, and dried to form a positive-tone resist pattern.

An optimum dose at which a 1:1 line-and-space (1L1S) pattern having a line width of 90 nm was formed was taken as the sensitivity. A scanning electron microscope ("S-9380" manufactured by Hitachi High-Technologies Corporation) was used for the measurement.

(4) Cross-Sectional Shape of Pattern (Pattern Shape)

The cross-sectional shape of the 90 nm line-and-space pattern (refer to (3)) was observed using a scanning electron microscope ("S-4800" manufactured by Hitachi High-Technologies Corporation). A case where the line-and-space pattern had a T-top shape (i.e., a shape other than a rectangular shape) was evaluated as "Bad", and a case where the line-and-space pattern had a rectangular shape was evaluated as "Good".

(5) Number of Defects

An 8-inch silicon wafer on which an underlayer antireflective film ("ARC29A" manufactured by Bruwer Science) (thickness: 77 nm) was formed, was used as a substrate. The antireflective film was formed using the above coater/developer.

The radiation-sensitive composition was spin-coated onto the substrate using the above coater/developer, and prebaked (PB) under conditions shown in Table 4 to form a resist film having a thickness of 120 nm. The resist film was rinsed with purified water for 90 seconds.

The resist film was exposed via a mask pattern using an ArF excimer laser exposure system ("NSR S306C" manufactured by Nikon Corp.) (NA=0.75, σ=0.85, ½ annular). The resist film was then rinsed with purified water for 90 seconds. After performing PEB under conditions shown in Table 4, the resist film was developed at 23° C. for 60 seconds using a 2.38 mass % tetramethylammonium hydroxide aqueous solution, washed with water, and dried to form a positive-tone resist pattern.

A hole pattern (width: 1000 nm) was formed over the entire wafer at an optimum dose at which a hole pattern having a width of 1000 nm was formed to obtain a defect detection wafer. A scanning electron microscope ("S-9380" manufactured by Hitachi High-Technologies Corporation) was used for the measurement.

The number of defects of the hole pattern (width: 1000 nm) was measured using a system "KLA2351" (manufactured by KLA Tencor Corp.). Defects measured using the system "KLA2351" were observed using a scanning electron microscope ("S-9380" manufactured by Hitachi High Technologies Corp.), and classified into a defect due to the resist and a defect due to foreign matter. A case where the number of defects due to the resist was 100 or more per wafer was evaluated as "Bad", and a case where the number of defects due to the resist was less than 100 per wafer was evaluated as "Good".

Note that the term "defect due to the resist" refers to a residual defect due to insufficient dissolution during development, a protrusion defect due to undissolved resin in the solvent, and the like, and the term "defect due to foreign matter" refers to a defect that occurs due to dust, uneven application, bubbles, or the like.

TABLE 3

| | Polymer (A) (parts) | Polymer (B) (parts) | Acid generator (C) (parts) | Nitrogen-containing compound (E) (parts) | Solvent (D) (parts) |
|---|---|---|---|---|---|
| Example 1 | A-1 (1) | B-1 (100) | C-1 (7.5) | E-1 (0.65) | D-1 (1500) D-2 (650) D-3 (30) |
| Example 2 | A-2 (1.5) | B-1 (100) | C-1 (7.5) | E-1 (0.65) | D-1 (1500) D-2 (650) D-3 (30) |
| Example 3 | A-3 (1.5) | B-1 (100) | C-1 (7.5) | E-1 (0.65) | D-1 (1500) D-2 (650) D-3 (30) |
| Example 4 | A-4 (2.5) | B-1 (100) | C-1 (7.5) | E-1 (0.65) | D-1 (1500) D-2 (650) D-3 (30) |
| Example 5 | A-5 (1) | B-1 (100) | C-1 (7.5) | E-1 (0.65) | D-1 (1500) D-2 (650) D-3 (30) |
| Example 6 | A-6 (1.5) | B-1 (100) | C-1 (7.5) | E-1 (0.65) | D-1 (1500) D-2 (650) D-3 (30) |
| Example 7 | A-1 (1.5) | B-2 (100) | C-2 (8.0) | E-1 (0.65) | D-1 (1500) D-2 (650) D-3 (30) |
| Example 8 | A-2 (2.5) | B-2 (100) | C-2 (8.0) | E-1 (0.65) | D-1 (1500) D-2 (650) D-3 (30) |
| Example 9 | A-3 (1.5) | B-2 (100) | C-2 (8.0) | E-1 (0.65) | D-1 (1500) D-2 (650) D-3 (30) |
| Example 10 | A-4 (2.5) | B-2 (100) | C-2 (8.0) | E-1 (0.65) | D-1 (1500) D-2 (650) D-3 (30) |
| Example 11 | A-5 (1.5) | B-2 (100) | C-2 (8.0) | E-1 (0.65) | D-1 (1500) D-2 (650) D-3 (30) |
| Example 12 | A-6 (2.5) | B-2 (100) | C-2 (8.0) | E-1 (0.65) | D-1 (1500) D-2 (650) D-3 (30) |
| Comparative Example 1 | — | B-1 (100) | C-1 (7.5) | E-1 (0.65) | D-1 (1500) D-2 (650) D-3 (30) |
| Comparative Example 2 | — | B-2 (100) | C-2 (9.6) | E-1 (0.65) | D-1 (1500) D-2 (650) D-3 (30) |

TABLE 4

| | Bake (temp./time) | PEB (temp./time) | Elution volume | Receding contact angle (°) | Sensitivity (mJ/cm$^2$) | Pattern shape | Number of defects |
|---|---|---|---|---|---|---|---|
| Example 1 | 110° C./60 sec | 105° C./60 sec | Good | 76.0 | 73.0 | Good | Good |
| Example 2 | 110° C./60 sec | 105° C./60 sec | Good | 75.2 | 70.0 | Good | Good |
| Example 3 | 110° C./60 sec | 105° C./60 sec | Good | 77.8 | 70.0 | Good | Good |
| Example 4 | 110° C./60 sec | 105° C./60 sec | Good | 71.8 | 61.0 | Good | Good |
| Example 5 | 110° C./60 sec | 105° C./60 sec | Good | 78.0 | 70.0 | Good | Good |
| Example 6 | 110° C./60 sec | 105° C./60 sec | Good | 79.0 | 61.0 | Good | Good |
| Example 7 | 110° C./60 sec | 125° C./60 sec | Good | 84.5 | 52.0 | Good | Good |
| Example 8 | 110° C./60 sec | 125° C./60 sec | Good | 82.5 | 49.0 | Good | Good |
| Example 9 | 110° C./60 sec | 125° C./60 sec | Good | 82.1 | 46.0 | Good | Good |
| Example 10 | 110° C./60 sec | 125° C./60 sec | Good | 80.3 | 43.0 | Good | Good |
| Example 11 | 110° C./60 sec | 125° C./60 sec | Good | 82.8 | 47.0 | Good | Good |
| Example 12 | 110° C./60 sec | 125° C./60 sec | Good | 81.0 | 44.0 | Good | Good |
| Comparative Example 1 | 100° C./60 sec | 105° C./60 sec | Bad | 61.0 | 70 | Good | Bad |
| Comparative Example 2 | 100° C./60 sec | 125° C./60 sec | Bad | 61.0 | 49 | Good | Bad |

As is clear from Table 4, when using the radiation-sensitive composition (Examples 1 to 12) including the novel fluorine-containing polymer ((A-1) to (A-12)), the elution volume upon contact with the immersion liquid during liquid immersion lithography was small, a high receding contact angle and an excellent pattern shape were obtained, and the number of defects was small. Therefore, the radiation-sensitive composition is expected to be advantageous for advanced lithography. When using the radiation-sensitive compositions of Comparative Examples 1 and 2, the elution volume upon contact with the immersion liquid during liquid immersion lithography was large, the receding contact angle was low, and a large number of defects were observed.

The above radiation-sensitive composition may be used for lithography that utilizes deep ultraviolet rays, X-rays, electron beams, or the like as a light source. In particular, the above radiation-sensitive composition may suitably be used as a resist for forming a resist film used for liquid immersion lithography.

The above fluorine-containing polymer may suitably be used as a polymer component of the above radiation-sensitive composition, and the above novel compound may suitably be used as a monomer for producing the repeating unit of the fluorine-containing polymer.

According to the embodiment of the present invention, the radiation-sensitive composition that includes the polymer produces an excellent pattern shape, and reduces the elution volume upon contact with an immersion liquid (e.g., water) during liquid immersion lithography. Moreover, the receding contact angle formed by the resulting resist film and the immersion liquid can be sufficiently increased, and occurrence of development defects can be suppressed.

The fluorine-containing polymer may suitably be used for the radiation-sensitive composition, and the novel compound may suitably be used as a monomer component for producing the fluorine-containing polymer.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive composition comprising:
a fluorine-containing polymer;
an acid-labile group-containing polymer differing from the fluorine-containing polymer; and
a solvent,
the radiation-sensitive composition including the fluorine-containing polymer in an amount of 0.1 to 40 parts by mass based on 100 parts by mass of the acid-labile group-containing polymer,
the fluorine-containing polymer comprising:
a first repeating unit derived from a compound shown by a following formula (1); and
a second repeating unit shown by a following formula (2), (1)

wherein $R^1$ represents a hydrogen atom, a methyl group, or a trifluoromethyl group, $R^2$ represents a methylene group, an ethylene group, a 1-methylethylene group, a 2-methylethylene group, a divalent alicyclic hydrocarbon group derived from bicyclo[2.2.1]heptane, bicyclo[2.2.2]octane, tricyclo[5.2.1.0$^{2.6}$]decane, tetracyclo[6.2.1.1$^{3.6}$.0$^{2.7}$]dodecane or tricycle[3.3.1.1$^{3.7}$]decane, or a derivative thereof, each of $R^3$ represents at least one of a monovalent alicyclic hydrocarbon group having 4 to 20 carbon atoms, a derivative thereof, and a linear or branched alkyl group having 1 to 4 carbon atoms, provided that two of $R^3$ may bond to form a divalent alicyclic hydrocarbon group having 4 to 20 carbon atoms or a derivative thereof together with the carbon atom that is bonded thereto, and X represents a linear or branched fluoroalkylene group having 1 to 20 carbon atoms, (2)

wherein $R^4$ represents a hydrogen atom, a methyl group, or a trifluoromethyl group, and each of $R^5$ represents at least one of a monovalent alicyclic hydrocarbon group having 4 to 20 carbon atoms, a derivative thereof, and a linear or branched alkyl group having 1 to 4 carbon atoms, provided that two of $R^5$ may bond to form a divalent alicyclic hydrocarbon group having 4 to 20 carbon atoms or a derivative thereof together with the carbon atom bonded thereto.

2. The radiation-sensitive composition according to claim 1, wherein the radiation-sensitive composition includes the fluorine-containing polymer in an amount of 0.5 to 35 parts by mass based on 100 parts by mass of the acid-labile group-containing polymer.

3. The radiation-sensitive composition according to claim 1, further comprising a photoacid generator.

4. The radiation-sensitive composition according to claim 1, wherein a content of the first repeating unit in the fluorine-containing polymer is from 5 to 50 mol % based on a total amount (=100 mol %) of repeating units included in the fluorine-containing polymer.

5. The radiation-sensitive composition according to claim 1, wherein a content of the first repeating unit in the fluorine-containing polymer is from 10 to 40 mol % based on a total amount (=100 mol %) of repeating units included in the fluorine-containing polymer.

6. The radiation-sensitive composition according to claim 1, wherein a content of the first repeating unit in the fluorine-containing polymer is from 15 to 30 mol % based on a total amount (=100 mol %) of repeating units included in the fluorine-containing polymer.

7. The radiation-sensitive composition according to claim 1, wherein $R^2$ represents a methylene group, an ethylene group, a 1-methylethylene group, or a 2-methylethylene group.

* * * * *